(12) United States Patent
Westfall et al.

(10) Patent No.: US 10,537,087 B2
(45) Date of Patent: Jan. 21, 2020

(54) DETECTION OF MASTITIS USING COMPARISON OF ORP

(71) Applicant: Geoffrey J. Westfall, Brooklyn, CT (US)

(72) Inventors: Geoffrey J. Westfall, Brooklyn, CT (US); John W. Lounsbury, Colton, NY (US)

(73) Assignee: Geoffrey J. Westfall, Brooklyn, CT (US)

( * ) Notice: Subject to any disclaimer, the term of this patent is extended or adjusted under 35 U.S.C. 154(b) by 441 days.

(21) Appl. No.: 15/395,948

(22) Filed: Dec. 30, 2016

(65) Prior Publication Data

US 2017/0191961 A1 Jul. 6, 2017

Related U.S. Application Data

(60) Provisional application No. 62/273,663, filed on Dec. 31, 2015.

(51) Int. Cl.
*G01N 27/416* (2006.01)
*A01J 5/007* (2006.01)
*A01J 5/013* (2006.01)

(52) U.S. Cl.
CPC ............... *A01J 5/007* (2013.01); *A01J 5/013* (2013.01)

(58) Field of Classification Search
CPC ...... A01J 5/00; A01J 5/007; A01J 5/01; A01J 5/013; A01J 5/0131; A01J 5/0133; A01J 5/0136; G01N 27/416; G01N 27/4168; G01N 27/4166
See application file for complete search history.

(56) References Cited

U.S. PATENT DOCUMENTS

| | | |
|---|---|---|
| 4,548,807 A | 10/1985 | Westfall et al. |
| 4,716,032 A | 12/1987 | Westfall et al. |
| 6,183,785 B1 | 2/2001 | Westfall |
| 7,234,414 B2 | 6/2007 | Claycomb et al. |
| 8,076,143 B2 | 12/2011 | Westfall |
| 8,967,083 B2 | 3/2015 | Hoey |
| 2010/0058989 A1* | 3/2010 | Ohman .................. G01N 33/04 119/14.08 |
| 2012/0115184 A1* | 5/2012 | Rinken ................. A01J 5/0131 435/34 |
| 2012/0155184 A1 | 6/2012 | Kang |

FOREIGN PATENT DOCUMENTS

| | | |
|---|---|---|
| WO | 0135728 A1 | 5/2001 |
| WO | 2011-040825 A1 | 4/2011 |

* cited by examiner

*Primary Examiner* — Gurpreet Kaur
(74) *Attorney, Agent, or Firm* — Holzer Patel Drennan

(57) ABSTRACT

Determining the quality of milk due to the presence of mastitis by monitoring the oxidation reduction potential (ORP) of the raw (unpasteurized) milk. The ORP of the milk is tested by a sensor placed into the milk soon after having been removed from the animal (e.g., cow) and prior to the milk being combined in a bulk tank with milk from other animals. The sensor can be positioned in the line carrying the milk from the cow, allowing real-time testing of the milk. Each mammary gland (e.g., quarter) is tested separately, and the ORP levels are compared. Any gland (e.g., quarter) having a level that deviates from the other levels by a predetermined amount is considered suspect for mastitis.

19 Claims, No Drawings

DETECTION OF MASTITIS USING COMPARISON OF ORP

CROSS-REFERENCE

This application claims priority to U.S. provisional application 62/273,663 filed Dec. 31, 2015 by Geoffrey Westfall and John Lounsbury titled "Detection of Mastitis Using Comparison of ORP," the entire disclosure of which is incorporated herein by references for all purposes.

BACKGROUND

As a result of traditional selective breeding methods, milk production in dairy cows far exceeds the requirements of the newborn calf. Because of udder size, position, and anatomic configuration for rapid removal of large volumes of milk, the mammary glands of dairy cows are especially prone to injury and infection. In particular, mastitis, an infection of the mammary gland, is common in milking dairy cows, sheep, goats, and other milk-producing animals.

Clinically, mastitis typically produces heat, swelling, tenderness and possible deformation of the udder. Although the milk from a mastitic udder is generally safe for human consumption, a major concern is the cost to producers. Mastitis causes a decrease in the amount and quality of milk produced by the infected cow. With decreased quality, the price obtained for the milk likewise decreases. In some instances, depending on the level of infection, the milk is completely unsuitable. When this occurs, there are more white blood cells, also called somatic cells, secreted into the milk. Milk having a somatic cell count (SCC) of over 750,000/ml is considered unsaleable in the U.S. Other countries have different acceptable levels of somatic cell count.

In most modern milking operations, the milk from all cows being milked at a facility is combined together for sale. Unfortunately, milk from one mastitic cow may sufficiently taint the quality of the entire volume of milk, and thus decrease the price obtained for the entire volume, possibly rendering unsaleable the entire volume of milk if the level of infection is sufficiently high.

A common test for the presence of mastitic infection is the California Mastitis Test (CMT). This test, however, is a manual test that takes several minutes and is very subject to interpretation. Electrical conductivity testing of the milk is also a common test used for the presence of mastitic infection. This method of mastitis detection, however, has not been reliable.

What is desired is a fast, cost efficient method for determining the presence, and extent, of any mastitis infection, prior to the milk from an infected cow being mixed with higher quality milk.

SUMMARY

The present disclosure relates to methods for determining the quality of milk due to the presence of mastitis by monitoring the oxidation reduction potential (ORP) of the raw (unpasteurized) milk from a single animal (e.g., cow). In accordance with the methods, the ORP of the milk from multiple glands (e.g., quarters) is tested by a sensor placed into the milk from each of the glands, preferably, soon after the milk is removed from the animal and prior to the milk being combined, e.g., in a bulk tank, with milk from other animals. The sensor is positioned in the line carrying the milk from each quarter the cow, allowing real-time testing of the milk. If an ORP measurement varies by at least 50 mV from the ORP measurement from the other quarters, that quarter is considered suspect of mastitis.

In some embodiments, if the rate of change of ORP measurement of the multiple quarters is compared. If the rate of change of ORP differs by at least 4×, that quarter is considered suspect of mastitis.

One particular embodiment described herein is a method that includes measuring the oxidation-reduction potential (ORP) of raw, unpasteurized milk from at least three quarters of a single animal, and comparing the at least three ORP measurements.

For example, a method an include measuring an ORP of milk from a first quarter of an animal, measuring an ORP of milk from a second quarter of the animal, measuring an ORP of milk from a third quarter of the animal, and comparing the ORP from the first quarter against the ORP of the second quarter and against the ORP of the third quarter. If one of the ORP's differs by 50 mV or more (e.g., 100 mV, 200 mV, 300 mV) than the other ORP's, considering that quarter suspect of mastitis. The method can further include measuring an ORP of milk from a fourth quarter of the animal, and comparing the ORP from the first quarter against the ORP of the fourth quarter.

Another particular embodiment described herein is a method that includes measuring the rate of change of oxidation-reduction potential (ORP) of raw, unpasteurized milk from at least three quarters of a single animal over time, and comparing the at least three ORP rates of change.

These and various other features and advantages will be apparent from a reading of the following detailed description.

DETAILED DESCRIPTION

The present disclosure describes methods for determining the quality of milk due to the presence of mastitis by monitoring the oxidation reduction potential (ORP) of the raw (unpasteurized) milk. The methods are suitable for use with milk from any milk producing mammals including, for example, cattle, sheep, goats, llamas, pigs, camels, etc. Because cattle are one of the most common milk-producing animals, the present methods are described with reference to dairy cattle. However, the methods should not be construed as being limited to use with cattle.

The oxidation-reduction potential (ORP) is the potential that a species has to either lose or acquire electrons, thus creating an electrical current that can be measured. Often, ORP may be alternately referred to with words and phrases such as "redox" and "redox state."

With these methods, raw, unpasteurized whole milk is tested. Typically, no additives are added to the milk prior to testing; that is, the milk is as it comes out from the animal. In some instances, the milk may be filtered to remove particulate matter (debris such as mud, straw, sand, etc. that is common on the teats of cows) prior to testing the milk.

As briefly described above, the present disclosure is directed to simple and efficient methods for qualitative monitoring for the presence of mastitic infection in a cow, by testing the ORP of her milk. This quantitative ORP level can then relate to the quality of the milk and translate to the eventual use of the milk.

Milk is composed of various fats, proteins, sugars, and numerous chemical ions. The specific level of these components in the milk varies from cow to cow, but is essentially unchanged from quarter to quarter in the same cow. Factors that affect these levels include, e.g., specific diet (e.g., some cows tend to favor and consume one ingredient of the feed mix more than another), water consumption, mineral block consumption, and genetics.

However, it is known that the concentrations of sodium and chloride ions in the milk increase and the concentrations of potassium and calcium ions in the milk decrease when a mastitic infection is present. No specific concentration or level of these ions in the milk of a healthy cow has been determined to be a threshold level for "normal". Likewise, no specific concentration or level of these ions has been determined to be a threshold level for an "infected" cow. Additionally, other ions, proteins, fats, lipids, enzymes, and other ingredients present in milk also increase or decrease with the presence of mastitic infection. Normal, healthy milk (which has a somatic cell count (SCC) in the area of about 100,000/ml and less), is very stable and non-reactive, and there is little to no change in the level and types of ions, fats, lipids, enzymes, etc. over time (after being withdrawn from the cow).

When mastitis (or other infection) is present, various proteases and lipases, due to the presence of a high level of white cells, attack and degrade various lipids and proteins in the milk. This degradation begins when the milk is still in the cow and continues even when the milk is refrigerated, resulting in a constantly decreasing milk quality. This highly reactive and changing milk quality can be seen in the ORP measurement, both the quantitative level (in mV) and in the rate of change of the ORP level over time (e.g., over 10 seconds).

It is rare to have mastitis present in more than one quarter at a time. Having one quarter infected, however, is not uncommon. The milk from each quarter is tested soon after having been removed from the animal (e.g., cow) and optimally prior to the milk being combined with milk from other animals, such as in a bulk tank. Raw, unpasteurized whole milk is tested.

Modern milking systems attach a hose or line to each teat, referred to as a short-milk tube, and apply a pulsatile vacuum to the teat so that the sphincter muscle is intermittently opened and closed to release the milk. Four short-milk tubes combine at a claw, where the milk from the quarters is combined and then flows through the line to the holding tank, where it is co-mingled with the milk from other cows. Together, the four short-milk tubes and the claw are referred to as a milking cluster.

An ORP sensor is installed in the short-milk tube, upstream of combining the four short-milk tubes at the claw, and upstream of the holding tank. As the milk is obtained from the quarter and passed through the short-milk tube, an ORP measured is obtained. The ORP measurement can be taken as soon as milk begins to flow, or the measurement may be delayed, e.g., 5-10 seconds. Depending on the sensor, the measurement itself may take, e.g., 10-20 seconds.

The measurements from the quarters are compared, and any outliers (e.g., by at least about 50 mV) are flagged as suspect for presence of mastitis. It has been found, as indicated above, the ions, enzymes and other components are essentially the same in healthy quarters of an animal, but an infected quarter will have, e.g., increased concentrations of sodium and chloride ions and decreased concentrations of potassium and calcium ions. These different ion concentrations produce an ORP measurement different than the ORP measurement from healthy quarters.

The difference in ORP measurement will be at least about 50 mV, in some embodiments at least 100 mV, in other embodiments at least 200 mV, and even as much as 300 mV, or more. The difference in mV may be either positive or negative. As an example, three quarters may have measurements of about 0 to +5 mV, while an infected quarter has a measurement of about +100 mV. As another example, three quarters may have measurements of about −10 to −20 mV, while an infected quarter has a measurement of about +50 mV. As yet another example, three quarters may have measurements of about +50 to +60 mV, while an infected quarter has a measurement of about −50 mV. Normal, healthy milk typically has an ORP in the range of −70 mV to +70 mV.

It has also been found that the rate of change in ORP, over time, is significantly greater for an infected quarter than a healthy quarter. The rate of change in ORP measurement will be at least about 4×, in some embodiments at least 5×, in other embodiments at least 6×, in other embodiments at least 7×, or 8×, or 9× and even as much as 10×, or more.

The second ORP measurement may be taken, for example, 10 seconds after the first measurement, in other examples, 20 seconds or 30 seconds. From the first and second measurements, the rate of change of ORP can be calculated. As an example, three quarters may have a rate of change of no greater than 2 mV over 10 seconds, while an infected quarter has a rate of change of 10 mV over 10 seconds (i.e., 5×). As another example, three quarters may have a rate of change of no greater than 1 mV over 10 seconds, while an infected quarter has a rate of change of 10 mV over 10 seconds (i.e., 10×).

Example methods include measuring the rate of change of oxidation-reduction potential (ORP) of raw, unpasteurized milk from at least three quarters of a single animal over time, and comparing the at least three ORP rates of change. If a rate of change for one quarter deviates by at least 4× from the other rates of change, the one quarter is considered suspect of mastitis. If a rate of change for one quarter deviates by at least 5× from the other rates of change, the one quarter is considered suspect of mastitis. If a rate of change deviates by at least 10× from the other measurements, that quarter is considered suspect of mastitis. The rate of change of ORP may be measured over 10 seconds, 15 seconds, or 20 seconds. For any and all, the method further includes discarding the milk from the one quarter if the one quarter is suspect of mastitis. The ORP can be measured in a short-line of a milking system or in a bulk tank line.

It has been found that the ORP level and the rate of change are highly dependent on the temperature of the sample, thus all samples from the animal should be stored together, if not tested upon being removed from the cow.

If milk from a quarter is suspect of being infected, the milk can be diverted to a holding tank or disposed, thus not mixing potentially poor quality milk with the other milk. By having a sensor in the short-milk tube, the infected quarter can be isolated, if it is suspect of infection.

At this time, no accurate, quantitative correlation has been made between ORP measurement or rate of change and SCC, however, future work may determine a correlation. An SCC of 200,000-350,000/ml is average for dairy cows, a level of 100,000/ml or less is considered to be especially good milk, and a level of 750,000/ml is the legal limit for acceptable milk.

The probe or sensor used for the ORP measurements is one that is suitable for milk and the various ingredients present in it. A high-speed sensor, which can provide an ORP value in less then 20 seconds (e.g., less than 10 seconds, less than 5 seconds) is preferred although not required. A stainless steel probe is particularly suited for milk, as stainless steel is an approved material for equipment in the dairy industry. An "open" probe, with a platinum sensor tip, is a suitable ORP probe to use. Because of the large molecules (e.g., enzymes, proteins, white blood cells, etc.) present in milk, a probe without a filter is preferred, as the large molecules may have a tendency to clog the filter or otherwise decrease the flow of milk to the sensor.

Various sensors are commercially available to measure the ORP. The sensor may be hard-wired to the computer, or may use RF or cellular communication mechanism to relay the ORP results to the computer. BlueTooth™ is a particularly suitable RF communication mode, as it is relatively short distance. The sensor may be configured to additionally detect the concentration of certain ions (e.g., $Na^+$, $Cl^-$, $K^+$, $Ca^+$), the pH, the temperature, or the like. The ORP can be measured, compared and/or recorded by the operator. Depending on the technology available, one could use a computerized system to automatically compare and/or record the measured values. The computerized system can be any suitable system, such as a computer, a tablet, a cell phone, etc.; in some implementations, the computerized system includes a display module to visually display the measured values or an error warning. A warning may be a textual error message, a light, an audible tone, or any combination thereof.

The system can be completely automated. The ORP sensor can relay the ORP results to a computer or other system, which can control valves, switches, and/or solenoids based on the results, thus switching among the milk lines and removing the questionable milk from the system.

Although not preferred, samples of milk can be tested manually, such as with a hand held ORP sensor, and then the ORP measurements compared, either manually or by computer.

The ORP values for an animal can be monitored from month to month in order to spot trends in her overall health.

The above specification and examples provide a complete description of the structure, features and use of exemplary embodiments of the invention. ORP measurements can be used to determine a quarter suspect of mastitic infection, either based on comparison of quantitative ORP levels or comparison of rate of change of ORP levels. Since many embodiments of the invention can be made without departing from the spirit and scope of the invention, the invention resides in the claims hereinafter appended. Furthermore, structural features of the different embodiments may be combined in yet another embodiment without departing from the recited claims.

What is claimed is:

1. A method comprising measuring the oxidation-reduction potential (ORP) of raw, unpasteurized milk from at least three quarters of a single animal, and comparing the at least three ORP measurements, wherein responsive to an ORP measurement from one quarter deviating by at least 50 mV from the at least other two ORP measurements, considering that one quarter suspect of mastitis.

2. The method of claim 1, wherein responsive to a measurement deviating by at least 100 mV from the at least other two measurements, considering that quarter suspect of mastitis.

3. The method of claim 1, wherein responsive to a measurement deviating by at least 200 mV from the at least other two measurements, considering that quarter suspect of mastitis.

4. The method of claim 1, wherein responsive to a measurement deviating by at least 300 mV from the at least other two measurements, considering that quarter suspect of mastitis.

5. The method of claim 1, further comprising discarding the milk from the one quarter if the one quarter is suspect of mastitis.

6. The method of claim 1, wherein the ORP is measured in a short-line of a milking system.

7. The method of claim 1, wherein the measuring is done within 10 seconds of attaching milking equipment to the quarter.

8. A system for detecting a probability of mastitis infection in a quarter, the system comprising:
   a milking apparatus comprising four short-milk tubes each having an ORP sensor in-line;
   a mechanism configured to measure the ORP of raw, unpasteurized milk from at least three quarters of a single animal, obtain the rate of change of the at least three ORP measurements, and compare the rates of change of the at least three ORP measurements, wherein responsive to the rate of change from one quarter deviating by at least 4× from the at least other two rates of change, considering that quarter suspect of mastitis;
   a line operably connecting the milking apparatus to a bulk tank; and
   a diverting system operably connected between the milking apparatus and the bulk tank to divert milk away from the bulk tank.

9. The system of claim 8, wherein the diverting system is connected to the line to the bulk tank.

10. The system of claim 8, wherein the diverting system is connected to each of the short-milk tubes.

11. The system of claim 8, wherein the mechanism is computer-based.

12. The system of claim 8, wherein the mechanism is manual.

13. The system of claim 8, wherein the ORP-sensor is connected to the mechanism wirelessly.

14. The system of claim 8, wherein the ORP-sensor is wired to the mechanism.

15. A method comprising measuring the oxidation-reduction potential (ORP) of raw, unpasteurized milk from at least three quarters of a single animal, obtaining the rate of change of the at least three ORP measurements, and comparing the rates of change of the at least three ORP measurements, wherein responsive to the rate of change from one quarter deviating by at least 4× from the at least other two rates of change, considering that quarter suspect of mastitis.

16. The method of claim 15, wherein responsive to the rate of change deviating by at least 5×, considering that quarter suspect of mastitis.

17. The method of claim 15, wherein responsive to the rate of change deviating by at least 6×, considering that quarter suspect of mastitis.

18. The method of claim 15, wherein responsive to the rate of change deviating by at least 10×, considering that quarter suspect of mastitis.

19. The method of claim 15, wherein the measuring is done within 10 seconds of attaching milking equipment to the quarter.

* * * * *